United States Patent [19]

Hadley et al.

[11] Patent Number: 5,043,342

[45] Date of Patent: Aug. 27, 1991

[54] OXADIAZOLYL BICYCLOHEPTANES FOR DEMENTIA TREATMENT

[75] Inventors: Michael S. Hadley; Paul A. Wyman; Barry S. Orlek, all of Harlow, England

[73] Assignee: Beecham Group p.l.c., Brentford, England

[21] Appl. No.: 454,170

[22] Filed: Dec. 21, 1989

[30] Foreign Application Priority Data

Dec. 23, 1988 [GB] United Kingdom ............... 8830226

[51] Int. Cl.$^5$ .................... A61K 31/44; C07D 221/02
[52] U.S. Cl. ..................................... 514/299; 546/112
[58] Field of Search ............... 546/209, 112; 514/326, 514/299

[56] References Cited

U.S. PATENT DOCUMENTS

| Re. 29,556 | 2/1978 | Adelstein | 546/209 |
|---|---|---|---|
| 2,658,067 | 11/1953 | Duschinsky | 260/294.3 |
| 3,419,575 | 12/1965 | Gries | 260/306.8 |
| 3,501,471 | 3/1970 | Remers et al. | 260/250 |
| 3,681,363 | 8/1972 | Elkin et al. | 260/293.53 |
| 4,038,402 | 7/1977 | Kaminka et al. | 424/267 |
| 4,203,990 | 5/1980 | Yen | 424/267 |
| 4,599,344 | 7/1986 | Morgan | 514/305 |
| 4,608,378 | 8/1986 | Falch et al. | 534/382 |
| 4,705,786 | 11/1987 | Yamamoto et al. | 546/193 |

FOREIGN PATENT DOCUMENTS

| 1419393 | 5/1983 | Australia . | |
|---|---|---|---|
| 0239309 | 9/1987 | European Pat. Off. | 546/209 |
| 0261763 | 3/1988 | European Pat. Off. | 546/209 |
| 0307141 | 3/1989 | European Pat. Off. . | |
| 0316718 | 5/1989 | European Pat. Off. . | |

OTHER PUBLICATIONS

K. A. Zaitseva et al, *Chem. Abs.;* vol. 62:11 (May 24, 1965); *Farmakol. i Toksikol;* 27:6, p. 686-690 (1964).
B. P. Thill et al., "Azabicyclic Alkohols. V., *Chem. Abs.;* vol. 70:11 (Mar. 17, 1969); *J. Org. Chem.,* 13:12, pp. 4376-4380 (1968).
H. S. Aaron et al., *J. Amer. Chem. Soc.,* 89, pp. 1431-1437 (1967).
G. Lambrecht and E. Mutschler, *Drug Res.,* 24, p. 1725 (1975).
C. A. Grob and E. Renk, *Helv. Chim. Acta.,* 37, p. 1689 (1954).
M. J. Martell and T. O. Soine, *J. Pharm. Sci.,* 52, pp. 331-336 (1963).
M. D. Mashkovsky, *Proc. 1st Int. Pharmacol. Meet.,* 7, pp. 359-3661 (1963).
D. Spry and H. S. Aaron, *J. Org. Chem.,* 34, pp. 3674-3676 (1969).
L. H. Sternbach and S. Kaiser, *J. Amer. Chem. Soc.,* 74, pp. 2219-2221 (1952) ("Sternbach-I").
L. H. Sternbach and S. Kaiser, *J. Amer. Chem. Soc.,* 74, pp. 2215-2218 (1952) ("Sternbach-II").
J. E. Christie et al., *Brit. J. Psychiat.,* 138, pp. 46-50 (1981).
P. T. Francis et al., *N. Engl. J. Med.,* 313, pp. 7-11 (1985).
E. Hollander et al., *Brit. Med. Bull.,* 42, pp. 97-100 (1986).
E. K. Perry et al., *Can J. Neurol. Sci.,* 13, pp. 521-527 (1986).
R. Peterson, *Psychopharmacology,* 52, pp. 283-289 (1977).
Sitaram et al., *Science,* 201, pp. 274 (1978).
J. Med. Chem. 29, 1004 (1986), Sauerberg et al.

*Primary Examiner*—Mary C. Lee
*Assistant Examiner*—Robert C. Whittenbaugh
*Attorney, Agent, or Firm*—Hopgood, Calimafde, Kalil, Blaustein & Judlowe

[57] ABSTRACT

A compound of formula (I) or a pharmaceutically acceptable salt thereof:

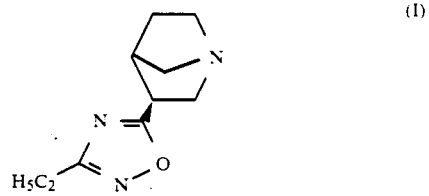

(I)

6 Claims, No Drawings

OXADIAZOLYL BICYCLOHEPTANES FOR DEMENTIA TREATMENT

This invention relates to compounds having pharmaceutical activity, to a process for their preparation and their use as pharmaceuticals.

EP-0261763 discloses a class of azabicyclic compounds having acetylcholine function enhancing activity.

A compound has now been discovered which enhances acetylcholine function via an action at muscarinic receptors within the central nervous system and is therefore of potential use in the treatment and/or prophylaxis of dementia in mammals.

Accordingly, the present invention provides a compound of formula (I) or a pharmaceutically acceptable salt thereof:

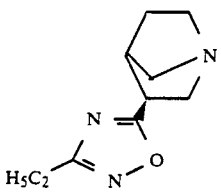

It will be understood that the compound of formula (I) has the stereo-chemical configuration in which the 3-ethyl-1,2,4-oxadiazol-5-yl group (hereinafter referred to as the group X) and the $CH_2$ bridge are on the same side of the plane of the molecule which contains both bridgehead atoms and the ring carbon atom bonded to the group X. This configuration will hereinafter be referred to as the exo configuration.

The compound of formula (I) is capable of existing in enantiomeric form. The invention extends to each of these stereoisomeric forms, and to mixtures thereof (including the racemate). The different stereoisomeric forms may be separated one from the other by the usual methods, for example using chiral resolving agents, or any given isomer may be obtained by stereospecific or asymmetric synthesis.

The compound of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The invention also provides a process for the preparation of a compound of formula (I), or a pharmaceutically acceptable salt thereof, which process comprises:

(a) cyclising a compound of formula (II):

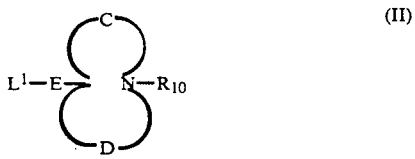

where $R_{10}$ is hydrogen or an N-protecting group, and either C is one, D is another and E is the remainder of $-(CH_2)_2-$, $-CH_2-$ and $-CHX'-CH_2-$ or groups convertible thereto, X' is X or a group convertible thereto and $L^1$ is a leaving group, or C is one and E is the other of $-(CH_2)_2-$ and $-CH_2-$ or groups convertible thereto and D represents $-CHX''-CH_2-$ where X'' and $L_1$ together represent $-COO-$, and thereafter, optionally or as necessary and in any appropriate order, converting C, D and E to $-(CH_2)_2-$, $-CH_2-$ and $-CHX'-CH_2-$, removing any $R_{10}$ protecting group, converting X. to X, separating stereoisomeric forms and/or forming a pharmaceutically acceptable salt, or (b) cyclising a compound of formula (III):

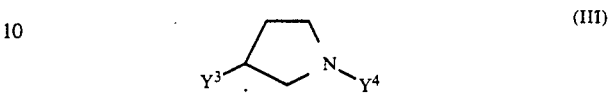

where $Y^4$ is $-(CH_2)m^{-W}$ and $Y^3$ is $-(CO)_qL^2$ where W is an electron withdrawing group, $L^2$ is a leaving group, m is 2 and q is 0 or and q are 1, and thereafter, optionally or as necessary and in any appropriate order, hydrolysir and decarboxylating the cyclisation product and converting the carbonyl group to CHX' where X' is X or a group convertible thereto, converting W to X' as defined, converting X' to X, separating sterecisomeric forms and/or forming a pharmaceutically acceptable salt.

Examples of leaving groups $L_1$ include halo such as chloro and hydroxy. Examples of $L^2$ include halo such as chloro or, when q is 1, $C_{1-4}$ alkoxy such as ethoxy. Examples of electron withdrawing groups W include $C_{1-4}$ alkoxycarbonyl and cyano. In the group $-CHX'-CH_2-$, examples of X' include hydroxy, cyano and carboxy ester.

In the process variant (a), where $L^1$ is hydroxy and D is $-CHOH-CH_2-$, the cyclisation may be carried out by pyrolysis, by the method of D.O. Spry and H.S. Aaron, J. Org. Chem., 1969, 34, 3674, to yield a compound where X is hydroxy.

Where E is $-COCH_2-$, the cyclisation may be carried out under basic conditions where $R_{10}$ is benzyl (F.I. Carrol, A.M. Ferguson, and J.B. Lewis, J. Org. Chem. 31, 2957, 1966). The resulting ketone may be reacted with tosylmethyl isocyanide to yield a compound where X' is cyano.

Where $L^1$ and X'' together represent $-CCO-$, the cyclisation is a rearrangement reaction which can be carried out under acid conditions in a polar solvent, such as hydrogen bromide in ethanol, at ambient temperature, to yield a compound where X' is a carboxy ester group. It is preferred to protect the nitrogen atom with an $R_{10}$ N-protecting group such as benzyl, which may be subsequently removed by hydrogenation over a suitable catalyst such as Pd/C.

In the process variant (b), where $Y^3$ and $Y^4$ both contain carboxy ester groups the cyclisation is a Dieckmann reaction which is catalysed by a base such as potassium t-butoxide at elevated temperature in a solvent such as toluene.

The resulting B-keto ester is hydrolysed and decarboxylated under conventional conditions such as heating at reflux in dilute hydrochloric acid.

The carbonyl group may then be reduced to an X' hydroxy group with a suitable reducing agent such as sodium borohydride in ethanol at ambient temperature, or sodium in ethanol at elevated temperature, such as the boiling point of the solvent, under an inert atmosphere such as nitrogen.

Alternatively, the carbonyl group may be converted directly to an X' cyano group with a suitable reagent such as tosylmethylisocyanide in an inert solvent such as dry dimethoxyethane, at depressed temperature, under basic conditions such as the presence of potassium t-butoxide.

Where q is 0, the cyclisation may be carried out as described in EP-0094742 under basic conditions such as sodium hydride and potassium t-butoxide, in an inert polar solvent such as dimethyl formamide.

Any endo isomer formed in the process of the invention can be converted to the exo isomer by appropriate means before final conversion of X' to X.

The conversions of the groups W and X' to X, may be carried out conventionally See for example standard text books on heterocyclic chemistry such as 'Comprehensive Heterocyclic Chemistry', A.R. Katritzky and C.W. Rees, Pergamon, 1984.

The X' or W group is first converted, as necessary, to a suitable starting group X' for the chosen conversion reaction to give the group X.

An X' hydroxy group may be converted to cyano by first converting it to a good leaving group such as mesyloxy or tosyloxy and then displacing it with cyanide ion.

An X' carboxy group may be obtained by conventional de-esterification of an X' or W alkoxycarbonyl group. Where $R_{10}$ is an N-protecting group and X' or W is a benzyloxycarbonyl group, the de-esterification and deprotection steps may conveniently be effected simultaneously by conventional hydrogeration such as described above. Alternatively, an X' carboxy group may be obtained by conventional acid or base hydrolysis of an X' or W cyano group.

An X' chlorocarbonyl group may be obtained by treatment of an X' carboxy group with thionyl chloride at elevated temperature.

An X' chlorocarbonyl group may be reacted with a propanoic acid amide oxime at elevated temperature in an inert, polar solvent such as chloroform, and the resulting substitution product cyclised at elevated temperature.

The invention also provides a process for the preparation of a compound of formula (I), or a pharmaceutically acceptable salt thereof, which process comprises reacting a compound of formula (IV):

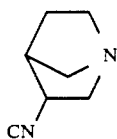

(IV)

to convert the cyano group into the group X as defined under formula (I), and thereafter, optionally forming a pharmaceutically acceptable salt.

Conversions of the cyano group are as described for conversions of X' cyano groups described above.

Intermediates of formulae (II), (III) and (IV) are known compounds (e.g. as described in EP-A-0094742) or may be prepared analogously.

Intermediates of formula (II) where X" and $L^1$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Intermediates of formula (II) where $L^1$ is a leaving group are described in, for example, Spry et al., J. Org. Chem., 1969, 34. 3674 and Hasse et al., Chem. Ber., 1960, 93. 1686.

Intermediates of formula (III) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50mg; and such unit doses may be administered more than once a day, for example two or three times a day, so that the total daily dosage is in the range of about 0.0to 10 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

The invention also provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

Description 1

(t) cis-4-Benzyl-2-oxo-2a, 3, 4, 5, 6, 6a -hexahydro-7H-furo[3,4-c]pyridine (D1)

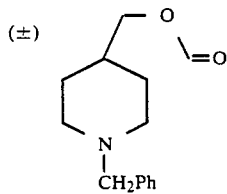

A solution of 2-oxo-7H-furo[3,4-c]pyridine+hydrochloride salt (9.43g, 0.055mole) in a mixture of ethanol (150ml), water (30ml) and 5M hydrochloric acid (5ml) was hydrogenated over 5% Pt/C (400mg) at 45° C. and 150 psi for 15h. The catalyst was filtered off through a pad of kieselguhr and the filtrate concentrated in vacuo. The residue was basified with saturated potassium carbonate solution and extracted with chloroform (3×70ml). The organic extract was dried (Na₂SO₄) and concentrated in vacuo to leave a brown oil (8.5g), which was dissolved in dry acetone (200ml) and treated with anhydrous potassium carbonate (16.5g) and benzyl bromide (7.2ml). The mixture was stirred at room temperature for 2h, then diluted with water (400ml) and extracted with ethyl acetate (3×150ml). The combined extracts were dried (Na₂SO₄) and concentrated in vacuo to give a brown oil, which was chromatographed on silica gel eluting with ether to give the title compound (D1) as a pale yellow oil (3.15g, 25%).

+J Kuthan, L. Musil, V. Jehlicka; Collection Czechoslov. Chem. Comm., 1977, 42, 283.

¹Nmr (CDCl₃)δ:
1.52–1.65 [1H, m, 6ax)
1.77–1.86 (1H, m, 6eq) 1.95 (1H, dt, 5ax, J=2.5Hz and J=13.5Hz) 2.31 (1H, dd, 3ax J=5Hz and J=13.5Hz)
2.42–2.52 (1H, m, 6a ax)
2.59–2.65 (1H, m, 2a eq)
2.66–2.73 (1H, m, 5eq)
3.21–3.28 (1H, m, 3eq)
3.45–3.62 (2H, m, CH₂Ph)
3.96–4.02 [1H, m, 1×CH₂OCO)
4.18–4.25 (1H, m 1×CH₂OCO)
7.20–7.34 (5H, m, PhCH₂)

DESCRIPTION 2

(±) exo-Ethyl1-benzyl-1-azoniabicyclo[2.2.1]heptane-3-carboxylate bromide (D2)

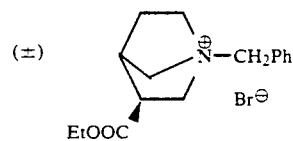

(±) cis-4-Benzyl-2-oxo-2a,3,4,5,6 6a-hexahydro-7H-furo[3,4-c]pyridine (D1, 2.80g, 0.012 mole) was treated with a saturated solution of hydrogen bromide in ethanol (150ml) and the mixture stirred at room temperature for 9 days. The mixture was concentrated in vacuo and the residue basified with saturated potassium carbonate solution then extracted with chloroform (3×80ml). The combined extracts were dried and concentrated in vacuo to give the title compound (D2) as a yellow gum (4.0g, 98%), which was used without purification.

DESCRIPTION 3

(±) exo-Metyvl 1-azabicyclo[2.2.1]heptane-3-carboxylate (D3)

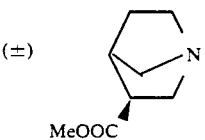

A solution of (±) exo-ethyl 1-benzyl-1-azoniabicyclo-[2.2.1]-heptane-3-carboxylate bromide (D2, 4.0g, 0.012mole) in ethanol (150ml) plus glacial acetic acid (2ml) was hydrogenated over 10% Pd/C (500mg) at atmospheric pressure and 40oC until uptake of hydrogen ceased. The catalyst was filtered off through a pad of kieselguhr and the filtrate concentrated in vacuo to leave a beige semi-solid, which was treated with 8M hydrochloric acid (70ml) and heated under reflux for 2h. The solution was concentrated in vacuo to give a beige solid, which was treated with methanolic hydrogen chloride (100ml) and heated under reflux for 30 minutes followed by 2 days at room temperature. The solution was concentrated in vacuo and the residue basified with saturated sodium hydrogen carbonate solution, then extracted with chloroform (3×60ml). The combined extracts were dried (Na$_2$SO$_4$) and concentrated to give an orange oil, which was distilled in a Kugelrohr apparatus (b.p. approx. 110–120° C. at 0.4mm) to give the title compound (D3) (1.3g, 70%) as a colourless oil. A portion was converted to its oxalate salt and recrystallised from methanol/ether, m.p. 134–136° C.

Oxalate:—1H Nmr (d$^6$DMSO)δ
1.65–1.76 j(1H, M) 1.90–2.05 (1H, m)
2.85–2.95 (1H, m)
2.95–3.15 (4H, m)
3 22–3.32 (1H, m)
3.35–3 50 (2H, m) 3.68 (3H, s, COOCH$_3$)
Analysis C$_8$H$_{13}$NO$_2$C$_2$H$_2$O$_4$
requires C: 48.98; H: 6.12; N: 5.71%
found: C: 48.97; H: 6.17; N: 5.51%
M.S.: Calculated mass for C$_8$H$_{13}$NO$_2$=155.0946 Observed mass =155.0946

DESCRIPTION 4

Propionamide Oxime (D4)

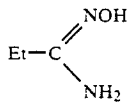

A solution of sodium methoxide (prepared from 2.30g, 0.10 mole of sodium) in methanol (40ml) was added dropwise over 10 minutes to a stirred solution of hydroxylamine hydrochloride (6.90g, 0.10 mole) in methanol (100ml). The mixture was stirred at room temperature for 1h, then the precipitate was filtered off and the filtrate treated with propionitrile (7.9ml, 0.11 mole) and heated under reflux for 12h. The clear solution was decanted from the white precipitate and concentrated in vacuo. The residue was dissolved in chloroform, filtered and concentrated in vacuo to give the title compound (D4) as a colourless oil (5.5g, 62%).

$^1$H Nmr (CDCl$_3$)δ:
1.12 (3H, t, J=7Hz)
2.12 (2H, q, J=7Hz)
4.60 (2H, br.s)
8.60 (1H, br.s)
Ir (film)υC=N 1655cm$^{-1}$ Example 1

(±) exo-3-(3-Ethyl-1,2,4-oxadiazol-5-yl)-1-azabicyclo-[2.2.1]heptane oxalate salt (E1)

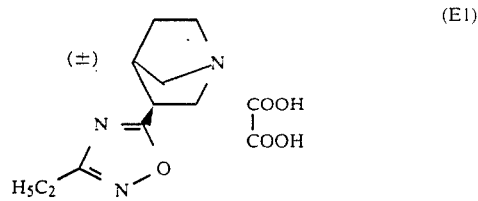

(±) exo-Methyl 1-azabicyclo[2.2.1]heptane-3-carboxylate (D3) (1.28g, 0.0083 mole) was treated with 8M hydrochloric acid (40ml) and heated under reflux for 1h. The solution was concentrated in vacuo to leave a white solid, which was treated with thionyl chloride (20ml) and stirred at room temperature for 4h. The solution was concentrated in vacuo and the residue dissolved in absolute chloroform (50ml), treated with propionamide oxime (D4) (800mg, 0.0090 mole) and the mixture heated under reflux for 18h. The reaction mixture was shaken with excess saturated potassium carbonate solution and the chloroform solution separated. The aqueous was extracted with chloroform (2×50ml) and all the chloroform solutions combined, dried (Na$_2$SO$_4$) and concentrated in vacuo to give a yellow oil.. This was purified by chromatography on silica gel eluting with 5% methanol/chloroform to give the title compound (E1) as a colourless oil. This was converted to its oxalate salt and recrystallised from methanol/ether to give a white solid (530mg, 23%) m.p 111–113° C.

Oxalate:—$^1$H Nmr (d$^6$—DMSO)δ:
1.23 (3H, t, J=7Hz)
1.70–1.85 (1H, m)
1.95–2.10 (1H, m) 2.73 (2H, q, J TM 7Hz)
3.05–3.20 (4H, m)
3.20–3.35 (1H, m)
3.50–3.70 (3H, m)
Analysis - C$_{10}$H$_{15}$N$_3$.C$_2$H$_2$O$_4$ requires C: 50.90, H: 6.05,
N 14.85; found C: 51 05, H: 6.05, N: 14.70 M.S.: — Calculated mass for C$_{10}$H$_{15}$N$_3$O=193.1215 Observed mass =193.1216

EXAMPLES 2 and 3

(+) exo-3-(3-Ethyl-1,2,4-oxadiazol-5-yl)-1-azabicyclo-[2.2.1]heptane oxylate salt (E2) and (-) exo-(3-Ethvl-1,2,4-oxadiazol-5-yl)-1-azabicyclo-[2.2.1]heptane oxalate salt (E3)

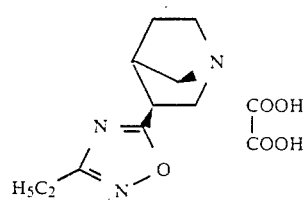

(+) (E2)
(-) (E3)

A solution of (±)exo-3-(3-ethyl-1,2,4-oxadiazol-5-yl)-1-azabicylco[2.2.1]heptane (E1) (1.58g, 0.0082mole) in methanol (15ml) was treated with (S)-(+)-1,1'-binaphthyl-2,2'-diyl hydrogen phosphate (2.0g, 0.0057 mole) and the resulting solution concentrated in vacuo to leave a colourless oil. This material was dissolved in hot acetone (90ml), diluted with ether (40ml) and left to stand at room temperature for 24h. The white crystalline solid was filtered off (1.27g) and recrystallised a further two times from a 2:1 acetone/ether mixture to give 690mg of white solid. This material was treated with excess 2M ammonium hydroxide solution and extracted twice with ethyl acetate. The combined extracts were dried ($Na_2SO_4$) and concentrated in vacuo to give a colourless oil, which was converted into its oxalate salt and recrystallised from methanol/ether to give the title compound (E2) (190mg) as a white solid m.p. 120–121° C.

Oxalate salt:—$[a]_D^{20} = +11.09°$ (c=1.01% in ethanol).

Purity of the enantiomer was confirmed as >95% by chiral shift $1_H$ Nmr.

The three mother liquors from the above recrystallisations were combined, concentrated in vacuo, the residue treated with excess 2M ammonium hydroxide solution and extracted twice with ethyl acetate. The combined extracts were dried ($Na_2SO_4$) and concentrated in vacuo to leave a pale yellow oil (1.32g), which was dissolved in methanol (20ml), treated with (R)−(−)−1,1'-binaphthyl-2,2'-diyl hydrogen phosphate (2.0g, 0.0057mole) and the resulting solution concentrated in vacuo to give a pale yellow oil. This material was dissolved in hot acetone (100ml), treated with ether (40ml) and left to stand at room temperature for 24h. The white crystalline solid was filtered off (2.44g) and recrystallised a further twice from a 2:1 acetone/ether mixture to give 1 07g of white solid. This material was treated with excess 2M ammonium hydroxide solution and extracted twice with ethyl acetate. The combined extracts were dried ($Na_2SO_4$) and concentrated in vacuo to leave a colourless oil, which was converted to its oxalate salt and recrystallised from methanol/ether to give the the title compound (E3) (355mg) as a white solid m.p. 120–121° C.

Oxalate salt:—$[a]_D^{20} = 11.5°$ (c=1.017% in ethanol).

Purity of the enantiomer was confirmed as >95% by chiral shift $^1$H Nmr.

BIOLOGICAL ACTIVITY

RADIO LIGAND BINDING

Cerebral cortex from Hooded Lister rats (Olac, UK) is homogenised in 2.5 vols ice-cold 50mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1ml aliquots at −20° C.

Incubations (total volume 2ml) are prepared using the above buffer with the addition of 2mM magnesium chloride in the 3H-Oxotremorine-M (3H-OXO-M) experiments. For 3H-Quinuclidinyl Benzilate (3H-QNB), 1ml of stored membranes is diluted to 30ml and 0. ml mixed with test compound and 0.27nM (c. 25,000 cpm) 3H-QNB (Amersham International). For 3H-OXO-M, 1ml of membranes is diluted to 6ml and 0.1ml mixed with test compound and 2nM (c. 250,000 cpm) 3H-OXO-M (New England Nuclear).

Non-specific binding of 3H-QNB is defined using 1μM Atropine sulphate (2μM Atropine) and of 3H-OXO-M using 10μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3 x 4ml ice-cold buffer. Radioactivity is assessed using a Packard BPLD scintillation counter, 3ml Pico-Fluor 30 (Packard) as scintillant.

This test provides an indication of the muscarinic binding activity of the test compound. The results are obtained as $IC_{50}$ values (i.e. the concentration which inhibits binding of the ligand by 50%) for the displacement of the muscarinic against 3H-OXO-M and the muscarinic antagonist 3H-QNB. The ratic $IC_{50}$(3H-QNB)/$IC_{50}$(3H-OXO-M) gives an indication of the agonist character of the compound. Agonists typically exhibit a large ratio; antagonists typically exhibit a ratio near to unity.

The results are shown in Table 1:

TABLE 1

| Compound* | [3H]-oxo-M $IC_{50}$ (nM) | [3H]-QNB $IC_{50}$ (nM) |
|---|---|---|
| E1 | 31 | 940 |
| E2 | 26 | 1590 |
| E3 | 36 | 725 |

*Tested as the oxalate salt

What is claimed is:

1. A compound of formula (I) or a pharmaceutically acceptable salt thereof:

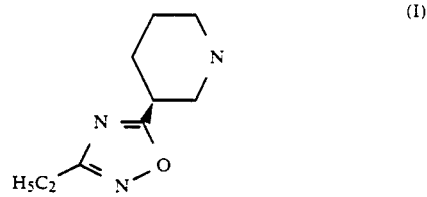

(I)

2. (±) exo-3-(3-Ethyl-1,2,4-oxadiazol-5-yl)-1azabicyclo[2.2.1]heptane or a pharmaceutically acceptable salt thereof.

3. (+) exo-3-(3-Ethyl-1,2,4-oxadiazol-5-yl)-1azabicyclo[2.2.1]heptane or a pharmaceutically acceptable salt thereof.

4. (−) exo-3-(3-Ethyl-1,2,4-oxadiazol-5-yl)-1azabicyclo[2.2.1]heptane or a pharmaceutically acceptable salt thereof.

5. A pharmaceutical composition for the treatment or prophylaxis of dementis which comprises an effective amount of a compound of formula (I) as defined in claim 1 or a pharmaceutically acceptable salt thereof, and a pharmaceutically acceptable carrier.

6. A method of treatment and/or prophylaxis of dementia in mammals including humans, which comprises administering to the sufferer an effective amount of a compound of formula (I) as defined in claim 1 or a pharmaceutically acceptable salt thereof.

* * * * *

UNITED STATES PATENT AND TRADEMARK OFFICE
CERTIFICATE OF CORRECTION

PATENT NO. : 5,043,342
DATED : August 27, 1991
INVENTOR(S) : Michael S. Hadley et al.

It is certified that error appears in the above-identified patent and that said Letters Patent is hereby corrected as shown below:

In claim 1, column 10, the structure of formula (I) should be as follows:

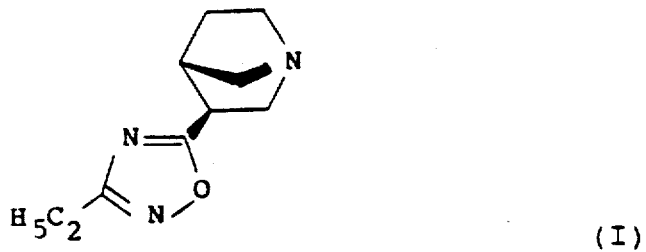

(I)

Claim 2, column 10, line 47, a hyphen (-) should be inserted before "azabicy-";

Claim 3, column 10, line 50, a hyphen (-) should be inserted before "azabicy-";

Claim 4, column 10, line 53, a hyphen (-) should be inserted before "azabicy-"; and

UNITED STATES PATENT AND TRADEMARK OFFICE
CERTIFICATE OF CORRECTION

PATENT NO. : 5,043,342

DATED : August 27, 1991

INVENTOR(S) : Michael S. Hadley, et. al.

It is certified that error appears in the above-identified patent and that said Letters Patent is hereby corrected as shown below:

Claim 5, line 57, "dementis" should be --dementia--.

Signed and Sealed this

Twenty-third Day of February, 1993

Attest:

STEPHEN G. KUNIN

*Attesting Officer*       Acting Commissioner of Patents and Trademarks